(12) United States Patent
Kodama

(10) Patent No.: US 10,661,067 B2
(45) Date of Patent: May 26, 2020

(54) INJECTION INSTRUMENT

(71) Applicant: TOPPAN PRINTING CO., LTD., Taito-ku (JP)

(72) Inventor: Yoshihiro Kodama, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 320 days.

(21) Appl. No.: 15/286,833

(22) Filed: Oct. 6, 2016

(65) Prior Publication Data

US 2017/0021152 A1 Jan. 26, 2017

Related U.S. Application Data

(63) Continuation of application No. PCT/JP2015/002011, filed on Apr. 9, 2015.

(30) Foreign Application Priority Data

Apr. 14, 2014 (JP) ................ 2014-083010

(51) Int. Cl.
*A61M 37/00* (2006.01)
*A61M 5/32* (2006.01)
(Continued)

(52) U.S. Cl.
CPC ........ *A61M 37/0015* (2013.01); *A61M 5/158* (2013.01); *A61M 5/3295* (2013.01);
(Continued)

(58) Field of Classification Search
CPC .............. A61M 5/14248; A61M 5/158; A61M 5/3287; A61M 5/3295; A61M 5/44;
(Continued)

(56) References Cited

U.S. PATENT DOCUMENTS 5,176,641 A * 1/1993 Idriss ................ A61M 5/14276
604/131
6,254,580 B1 * 7/2001 Svedman ........... A61B 10/0045
604/115
(Continued)

FOREIGN PATENT DOCUMENTS

JP 2003-534881 A 11/2003
JP 2005-21677 A 1/2005
(Continued)

OTHER PUBLICATIONS

International Search Report dated Jul. 14, 2015 in PCT/JP2015/002011, filed Apr. 9, 2015.

*Primary Examiner* — Shefali D Patel

(74) *Attorney, Agent, or Firm* — Oblon, McClelland, Maier & Neustadt, L.L.P.

(57) ABSTRACT

An injection instrument including a hollow needle body including a substrate having a first surface and a second surface opposite to the first surface, the hollow needle body having at least one projection which is formed on the first surface and has a through hole penetrating from a distal end of the at least one projection to the second surface of the substrate, a deforming member positioned outside a region where the at least one projection is formed, the deforming member being deformable to bulge in a bulging direction along a projecting direction of the at least one projection beyond a plane flush with the first surface, and a pressure channel through which a fluid is supplied such that a fluid pressure is applied to the deforming member. The deforming member is deformable in the bulging direction in response to the fluid pressure.

20 Claims, 7 Drawing Sheets

(51) Int. Cl.
*A61M 5/158* (2006.01)
*A61M 5/46* (2006.01)
*A61M 5/44* (2006.01)
*A61M 5/142* (2006.01)

(52) U.S. Cl.
CPC ............ *A61M 5/3298* (2013.01); *A61M 5/44* (2013.01); *A61M 5/46* (2013.01); *A61M 5/14248* (2013.01); *A61M 37/00* (2013.01); *A61M 2005/1583* (2013.01); *A61M 2037/003* (2013.01); *A61M 2037/0023* (2013.01)

(58) Field of Classification Search
CPC .......... A61M 5/46; A61M 2005/14252; A61M 2005/1583; A61M 2005/1585; A61M 37/00; A61M 37/0015; A61M 2037/0023; A61M 2037/003; A61M 2205/0216; A61M 2205/36; A61M 2205/3606
See application file for complete search history.

(56) References Cited

U.S. PATENT DOCUMENTS

| | | | |
|---|---|---|---|
| 6,436,078 B1* | 8/2002 | Svedman | A61B 5/14521 604/289 |
| 6,440,096 B1* | 8/2002 | Lastovich | A61B 17/205 424/448 |
| 6,537,242 B1* | 3/2003 | Palmer | A61M 37/0015 600/309 |
| 6,611,707 B1* | 8/2003 | Prausnitz | A61B 5/14514 604/21 |
| 6,623,457 B1* | 9/2003 | Rosenberg | A61B 17/205 604/191 |
| 7,842,008 B2 | 11/2010 | Clarke et al. | |
| 8,007,466 B2* | 8/2011 | Yeshurun | A61M 5/32 604/115 |
| 8,109,904 B1* | 2/2012 | Papp | A61M 25/10 604/103.01 |
| 8,419,684 B2 | 4/2013 | Clarke et al. | |
| 9,452,257 B2 | 9/2016 | Clarke et al. | |
| 2003/0187395 A1* | 10/2003 | Gabel | A61M 5/14248 604/134 |
| 2004/0044308 A1* | 3/2004 | Naimark | A61M 25/10 604/103 |
| 2004/0098014 A1* | 5/2004 | Flugelman | A61B 17/320725 606/192 |
| 2004/0138643 A1* | 7/2004 | Seward | A61L 29/16 604/507 |
| 2005/0177113 A1* | 8/2005 | Bertheas | A61M 5/158 604/192 |
| 2007/0213761 A1* | 9/2007 | Murphy | A61B 17/320725 606/194 |
| 2007/0219480 A1* | 9/2007 | Kamen | G05D 7/0647 604/20 |
| 2008/0015494 A1* | 1/2008 | Santini, Jr. | A61M 5/1409 604/65 |
| 2008/0091226 A1* | 4/2008 | Yeshurun | A61B 10/0045 606/186 |
| 2009/0054842 A1* | 2/2009 | Yeshurun | A61M 37/0015 604/173 |
| 2009/0118662 A1* | 5/2009 | Schnall | A61M 37/0015 604/20 |
| 2011/0104060 A1* | 5/2011 | Seward | A61K 9/0019 424/9.1 |
| 2011/0238154 A1* | 9/2011 | Murphy | A61B 17/32072 623/1.15 |
| 2011/0295230 A1* | 12/2011 | O'Dea | A61M 37/0015 604/506 |
| 2012/0041412 A1* | 2/2012 | Roth | A61M 25/10 604/500 |
| 2013/0041265 A1 | 2/2013 | Sostek et al. | |
| 2013/0060229 A1* | 3/2013 | Herman | A61M 25/1011 604/506 |
| 2013/0317476 A1* | 11/2013 | Searle | A61M 25/0045 604/506 |
| 2015/0080844 A1* | 3/2015 | Donovan | A61M 5/16854 604/505 |
| 2015/0217101 A1* | 8/2015 | Sumida | A61M 37/0015 604/173 |

FOREIGN PATENT DOCUMENTS

| | | |
|---|---|---|
| JP | 2008-154849 A | 7/2008 |
| JP | 2009-516572 A | 4/2009 |
| JP | 2014-18431 A | 2/2014 |

\* cited by examiner

INJECTION INSTRUMENT

CROSS-REFERENCE TO RELATED APPLICATIONS

The present application is a continuation of International Application No. PCT/JP2015/002011, filed Apr. 9, 2015, which is based upon and claims the benefits of priority to Japanese Application No. 2014-083010, filed Apr. 14, 2014. The entire contents of these applications are incorporated herein by reference.

BACKGROUND OF THE INVENTION

Field of the Invention

The present invention relates to an injection instrument.

Discussion of the Background

As a medicine administration method that is an alternative to an injection, there is a method, for example, of directly administering a medicine into the skin by puncturing the skin using an array component configured by a number of micron-order needle bodies as described in Patent Literature 1. Such a needle body is, for example, a hollow type needle body provided with a through hole (hereinafter also referred to as a "hollow needle body").

When a medicine is administered by means of an administration method using hollow needle bodies, a portion of the medicine is likely to leak to the surface of the skin during the administration, that is, liquid leakage might occur. As a measure against the liquid leakage, for example, Patent Literature 2 describes an injection drug delivery device including a needle, a limiter, and a rigid stabilizer. The limiter controls an insertion depth of the needle, and the rigid stabilizer prevents distortion, pressure contraction, or thinning of a tissue in the vicinity of the needle inserted site.

Patent Literature 1: JP-A-2005-021677
Patent Literature 2: JP-A-2009-516572

SUMMARY OF THE INVENTION

According to one aspect of the present invention, an injection instrument including a hollow needle body including a substrate having a first surface and a second surface opposite to the first surface, the hollow needle body having at least one projection which is formed on the first surface and has a through hole penetrating from a distal end of the projection to the second surface of the substrate, a deforming member (it may also be referred as deforming part) positioned outside a region where the at least one projection is formed, the deforming member being deformable to bulge in a bulging direction along a projecting direction of the projection beyond a plane flush with the first surface, and a pressure channel through which a fluid is supplied such that a fluid pressure is applied to the deforming member. The deforming member is deformable in the bulging direction in response to the fluid pressure.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
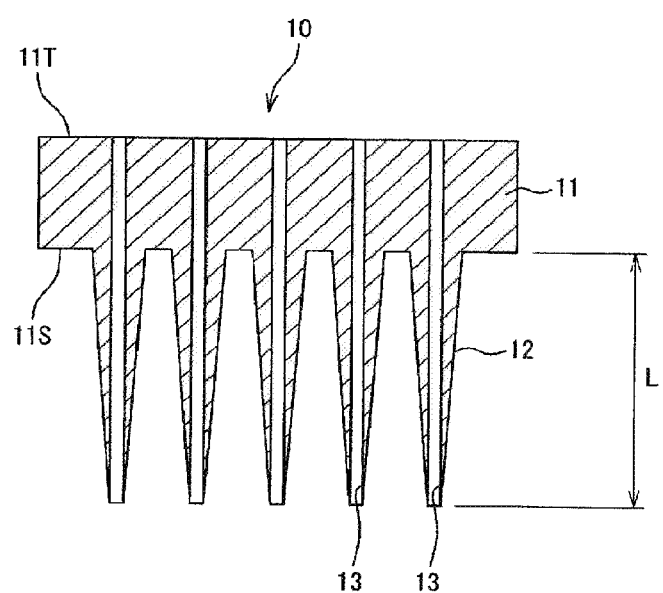
FIG. 1 is a schematic cross-sectional view of a hollow needle body of an injection instrument according to an embodiment of the present invention.

The embodiments will now be described with reference to the accompanying drawings, wherein like reference numerals designate corresponding or identical elements throughout the various drawings. In the following detailed description, many specific details are described in order to provide complete understanding of the embodiment of the present invention. However, it is obvious that one or more embodiments can be implemented without these specific details. Additionally, well-known structures and devices are schematically illustrated to simplify the drawings.

<Hollow Needle Body>

As illustrated in FIG. 1, a hollow needle body 10 constituting an injection instrument of the present embodiment includes a plurality of projections 12 on a first surface 11S of a plate-like substrate 11. A through hole 13 penetrating from a distal end of the projection 12 to a second surface 11T that is the other surface of the substrate 11 is formed in each of the projections 12. The through hole 13 serves as a path for a medicine injection, and a medicine is guided from the second surface 11T to the distal end of the projection 12 on the first surface 11S.

FIG. 1 illustrates that a plurality of projections 12 is formed on the substrate 11. Alternatively, only a single projection may be formed on a single substrate 11. The hollow needle body 10 is preferably configured such that the plurality of projections are perpendicularly provided on the single substrate 11, and the plurality of projections are arrayed. A medicine dose per puncture is expected to increase when a plurality of projections 12 are provided. In the case where the dose is prescribed, administration can be performed in a shorter time by using the plurality of projections 12. The term "arrayed" used herein refers to a state where the projections 12 are arranged in a specific pattern, and this state includes, for example, a grid pattern, a close-packed pattern, a concentric pattern, and a random pattern in plan view. The projection 12 preferably has a height L in the range of 0.3 mm or more to 2.0 mm or less. When the height L of each projection 12 is within the above-mentioned numerical range, the projection 12 does not reach nerve cells in a dermic layer, whereby pain felt by a patient at the time of puncturing the skin can be reduced.

A shape of the projection 12 is preferably a conic solid shape or the like, a cross-sectional area of which is reduced toward the distal end. Specific examples include conic solid shapes such as a cone and a pyramid. Alternatively, it is also possible to select a shape such as a pencil shape (a body part has a columnar shape and a distal end part has a conical shape) by combining a conic solid shape with a columnar shape such as a cylinder or a prism. A constriction or a step may be appropriately formed in a side surface of each projection 12. In FIG. 1, an outlet of the through hole 13 is formed at the top of the projection 12. Alternatively, the outlet of the through hole 13 may be formed in the side surface of the projection 12.

A material having biocompatibility is desirable as a material for the hollow needle body 10. Examples of the material having biocompatibility include: metals such as stainless steel, titanium, manganese, and silicon; ceramics such as alumina, zirconia, silicon carbide, and silicon nitride; and resins such as medical silicone, polylactic acid, polyglycolic acid, and polycarbonate.

The hollow needle body 10 can be manufactured using various known techniques. For example, in the case where a resin is used as the material, a hollow needle body 10 without a through hole or with a non-through hole is formed by means of a forming technique such as injection, extrusion, imprinting, hot embossing, and casting, followed by forming the through hole 13 by means of a micro drill, a laser or the like. Alternatively, for example, the through hole can be formed during a forming process such as injection, extrusion, imprinting, hot embossing, or casting.

<Injection Instrument>

Next, the injection instrument of the present embodiment will be described.

Figure 2:
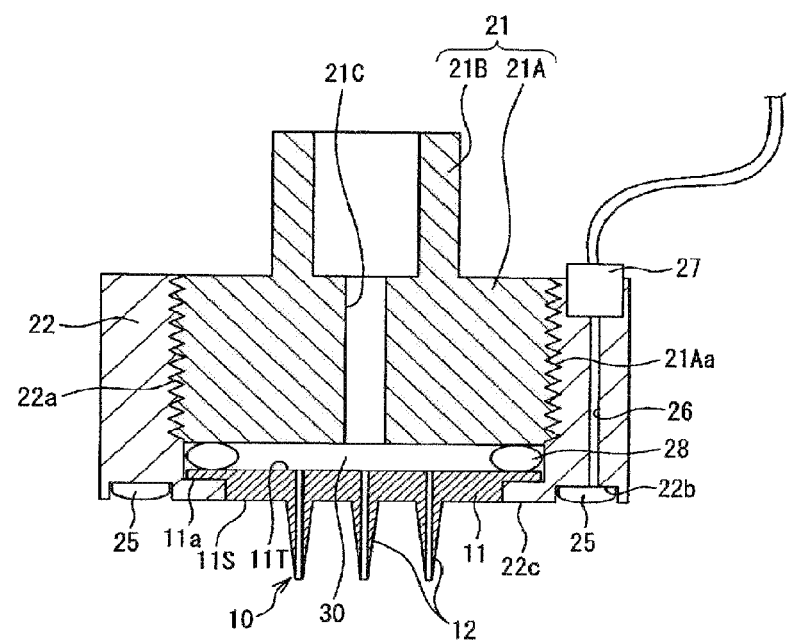
FIG. 2 is a schematic cross-sectional view of the injection instrument according to the embodiment of the present invention.

As illustrated in FIG. 2, the injection instrument of the present embodiment includes, the hollow needle body 10 described above, a holder 21, and an outer peripheral member 22. The injection instrument may include liquid tight members in various portions as necessary.

Figure 3:
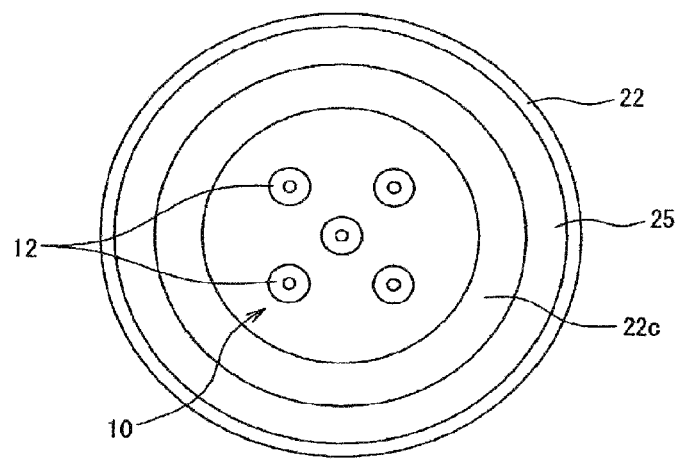
FIG. 3 is a schematic bottom view of the injection instrument according to the embodiment of the present invention.

As illustrated in FIG. 3, the substrate 11 of the hollow needle body 10 is formed in a disk-like shape and the thickness of a first surface side (lower surface side) outer peripheral edge portion is reduced to form a step.

The holder 21 has a holder body 21A having a columnar shape. The holder body 21A has an opposite surface (upper surface) that is opposite to a surface facing the hollow needle body 10. On the opposite surface, a connection part 21B formed of a cylindrical body having a diameter smaller than that of the holder body 21A is coaxially and integrally formed. A medicine channel 21C is formed in the holder body 21A and the connection part 21B penetrating a central part thereof in an axis direction. The holder body 21A has an outer diameter slightly larger than an outer diameter of the hollow needle body 10 in order to receive the hollow needle body 10.

Figure 4:
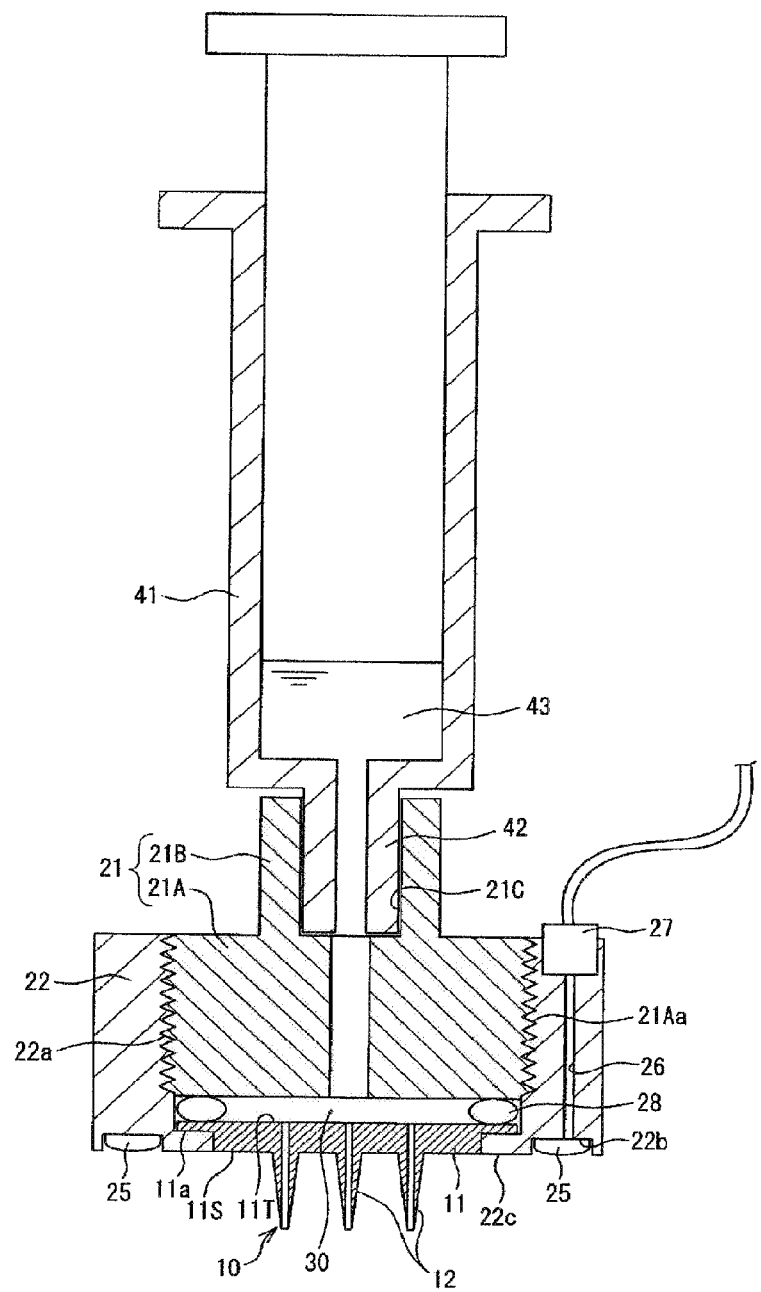
FIG. 4 is a schematic cross-sectional view schematically illustrating the injection instrument according to the embodiment of the present invention combined with a conventional injector.

The connection part 21B is designed in preparation for connection to generally used connection members and accordingly has a structure, for example, as illustrated in FIG. 4, enabling attachment/detachment of an injection needle attachment projection 42, as a connection member, of an injector 41 thereto/therefrom. The connection part 21B can guide an intracorporeal injection liquid (medicine) from the connection member side, via the medicine channel 21C, to a chamber 30 formed between the holder body 21A and the substrate 11. As a more specific example, the connection part 21B preferably has a tapered shape conforming to a luer lock standard.

The holder body 21A has an outer surface where a male screw 21Aa is formed.

As illustrated in FIGS. 2 and 3, the outer peripheral member 22 is formed of a thick cylindrical member. The outer peripheral member 22 has a hollow needle body 10 side lower end where an inward flange 22c is formed. The inward flange 22c can be fit to a step 11a formed on an outer periphery of the substrate 11. When the inward flange 22c is fit to the step 11a, the first surface 11S of the substrate 11 and a lower end surface of the outer peripheral member 22 are preferably flush with each other. The term "flush" as used herein means that the first surface 11S of the substrate 11 and the lower end surface of the outer peripheral member 22 are in the same plane.

The outer peripheral member 22 has an inner diameter slightly larger than the outer diameter of the hollow needle body 10 so that the hollow needle body 10 can be inserted from above. The outer peripheral member 22 has an inner surface where a female screw 22a is formed so as to be threadably engaged with the male screw 21Aa of the holder body 21A.

As illustrated in FIGS. 2 and 3, the hollow needle body 10 is mounted to the outer peripheral member 22 from above, and then the holder body 21A is attached to the outer peripheral member 22. For example, a liquid tight member 28 such as an O-ring is interposed between the holder body 21A and the hollow needle body 10. Specifically, as illustrated in FIG. 2, the holder body 21A is assembled to the outer peripheral member 22, whereby a connection surface can be kept liquid-tight. A structure for detachably arranging the holder body 21A and the outer peripheral member 22 can be achieved by the combination of the female screw 22a and the male screw 21Aa as described above. Alternatively, various other known detachable arrangement structures may be employed, examples of which include a snap coupling structure, an independent fixing screw, a combination of an independent fixing screw with a pressing plate, and the like. The liquid tight member 28 also plays a role of regulating displacement of the hollow needle body 10 in an (upward) direction of the outer peripheral member 22.

The outer peripheral member 22 is provided with a deforming part 25 and a pressure channel 26. The shape of the deforming part 25 can be deformed by the admission of a fluid. The pressure channel 26 is configured to cause a fluid to flow into the deforming part 25.

In the lower end surface of the outer peripheral member 22, a recess 22b is formed in a ring shape so as to be concentric with the substrate 11, and the deforming part 25 is mounted to the recess 22b so as to extend along an extension direction of the recess 22b. The deforming part 25 is formed, for example, of a film material body having elasticity, and has an upper surface that can receive a fluid.

The pressure channel 26 extends vertically within the outer peripheral member 22, with a lower end opening confronting the inside of the recess 22b. A plurality of pressure channels 26 may be formed. A reference sign 27 indicates a valve for adjusting a flow rate in the channel. The valve 27 does not have to be necessarily provided. The fluid to be supplied to the pressure channel 26 may be used in combination with a mechanism for forcibly sucking and discharging the fluid by use of a pump (not illustrated) separately provided outside the outer peripheral member 22. When the fluid is supplied to the recess 22b through the pressure channel 26, the deforming part 25 is elastically deformed in accordance with the pressure of the fluid, and the deforming part 25 bulges downward. Thus, the deforming part 25 bulges downward by an amount corresponding to the fluid pressure.

Since the pressure channel 26 is formed on an outer peripheral side of the medicine channel 21C, the degree of freedom is high in the arrangement of the channel relative to the deforming part.

The fluid to be supplied to the pressure channel 26 includes a gas and a liquid. Examples of the gas that can be used include various industrial gases, as well as compressed air, nitrogen gas, oxygen gas, and argon gas. Examples of the liquid that can be used include various organic solvents, as well as pure water, aqueous solution, alcohol, and oil.

Temperature may be controlled by the fluid to be injected, which may impart an effect of accelerating relaxation of the skin. More specifically, a warming medium fluid with a temperature of 25 degrees to 50 degrees or a cooling medium fluid with a temperature of 24 degrees to −10 degrees may be used.

The medium may be admitted into the pressure channel 26 after being warmed or cooled to an extent that the material forming the outer peripheral member 22 is not broken and a puncture target is not harmed. The warming medium and the cooling medium may be used so as to be alternately admitted into the pressure channel 26.

In the case where the fluid that is admitted into the pressure channel 26 is a warming medium, the relaxation of the skin can be accelerated. Therefore, swelling of the skin at the time of injecting the liquid can be accelerated. On the other hand, in the case where the fluid that is admitted into the pressure channel 26 is a cooling medium, an effect of tensing the skin is imparted. Therefore, the injection instrument according to an embodiment of the present invention can be reliably punched into the skin.

In configuring the deforming part 25, a material having stretchability is preferably used, and more specifically, various elastomers may be used. However, if the deforming part 25 is uniformly configured, the deforming part 25 swells uniformly in vertical and horizontal directions when the fluid is admitted into the deforming part 25, and might change into a form that is not sufficiently expanded/contracted in a necessary direction. Therefore, the deforming part 25, when designed with a difference in shape or material to provide an asymmetric structure, can be expanded/contracted in an arbitrary direction. More specifically, the expansion/contraction in an arbitrary direction is enabled in such a manner that a portion of the deforming part 25 is selectively thickened, or a material having low stretchability is used in a part where expansion is desired to be minimized. A sticky member may be carried on a surface of the deforming part 25, whereby an intimate contact with a puncture target can be enhanced at the time of puncture.

The deforming part 25 can be satisfactorily configured by weaving a low-stretchability material into a bellows structure, other than using a material having stretchability. In brief, the deforming part 25 only needs to have a configuration of being deformed and bulged downward by the fluid pressure of the fluid that is admitted into the pressure channel 26. The deforming part 25 bulges downward with a pressure corresponding to the fluid pressure.

The material forming the injection instrument of the present invention is not particularly limited. Examples of the material include plastic, glass, ceramic, metal, an elastomer and the like. In particular, examples of the plastic include polyethylene, polypropylene, polystyrene, polyamide, polycarbonate, a cyclic polyolefin, acrylic, a urethane resin, and an epoxy resin, and the like. Usable elastomers include natural rubber, nitrile rubber, butadiene rubber, silicone rubber, and the like.

The liquid tight member 28 is an annular member housed between the holder body 21A and the hollow needle body 10, and served by, for example, a member made up of an elastic body such as an O-ring mentioned above, or a member called a gasket. The liquid tight member 28 surrounds all the openings of the aforementioned plurality of through holes 13 of the hollow needle body 10 on the other surface of the hollow needle body 10.

A desired amount of intracorporeal injection liquid (e.g., a medicinal solution or a vaccine to be injected into an intradermal layer of an animal or a human) may be sucked into an internal space of an outer cylinder of the injector 41 via the through hole of the injection needle attachment projection 42, retained and used. Generally used injectors are easily available at a moderate price. The outer cylinder of a generally used injector is substantially transparent so that the amount of intracorporeal injection liquid retained inside can be visually checked from outside. Moreover, a scale for clearly indicating the amount of the liquid is provided on an outer surface of the outer cylinder. Therefore, by using such a generally used injector, the amount of intracorporeal injection liquid (medicine) 43 retained in the internal space of the outer cylinder thereof can be easily and precisely changed.

In this kind of mode, a portion that is in contact with the intracorporeal injection liquid 43 needs to be covered with or formed of a substance that does not denature the intracorporeal injection liquid 43 or is not denatured by the intracorporeal injection liquid.

(Usage Example or the Like)

Next, with reference to FIGS. 5 and 6, a procedure of using the injection instrument according to the embodiment configured as mentioned above will be described.

Figure 5:
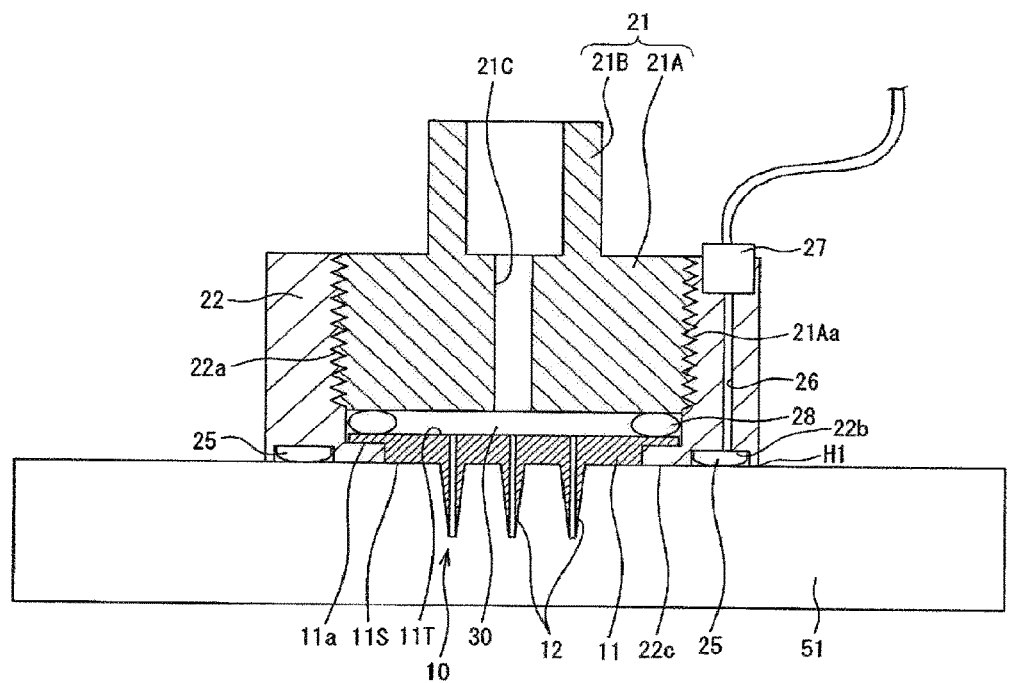
FIG. 5 is a schematic cross-sectional view of the injection instrument according to the embodiment of the present invention before fluid is admitted into the injection instrument.
Figure 6:
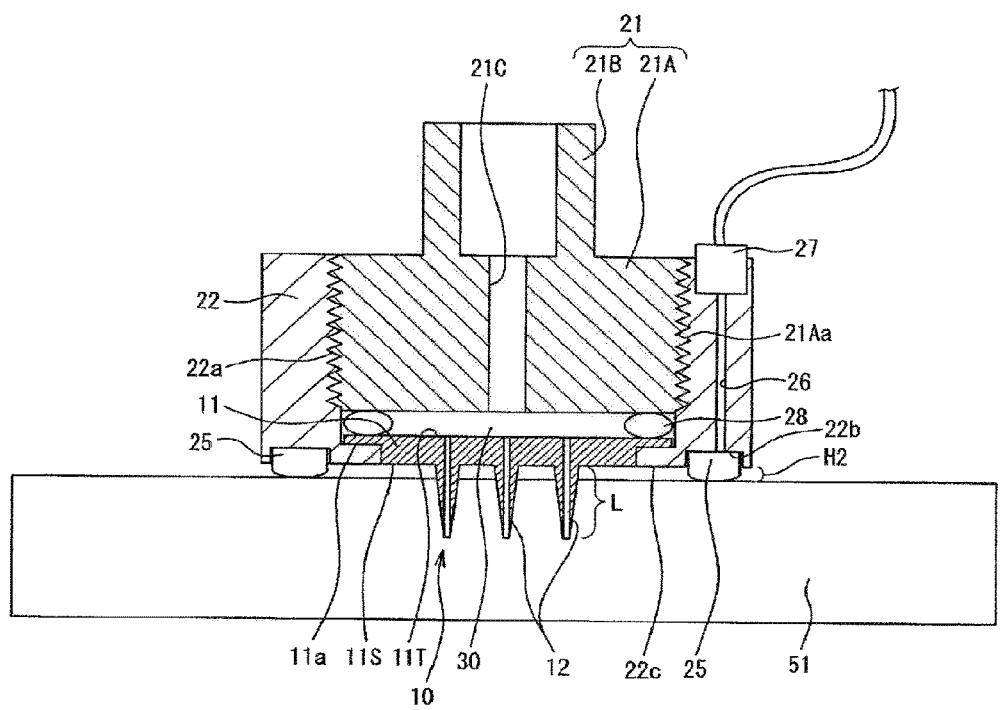
FIG. 6 is a schematic cross-sectional view of the injection instrument according to the embodiment of the present invention after fluid is admitted into the injection instrument.

FIGS. 5 and 6 illustrate the states of an injection instrument before and after fluid is admitted into the pressure channel 26. The injection instrument of the present embodiment is configured such that when a fluid is admitted into the pressure channel 26, the deforming part 25 swells and a position relative to a puncture direction can be changed.

The injection instrument shown in FIG. 5 is in a state where there is no admission of fluid and the deformation rate of the deforming part 25 is a minimum. The injection instrument shown in FIG. 6 is in a state after admission of the fluid where the deformation rate of the deforming part 25 is a maximum.

The injection instrument of the present embodiment is characterized in that a deformation distance caused by the deforming part 25 can be changed between a distance H1 and a distance H2. Each of the H1 and the H2 indicates a distance between the first surface 11S of the hollow needle body 10 and a puncture target 51. Therefore, FIG. 5 illustrates a state that H1=0 mm is established. The distance can be changed from H1 to H2 by controlling the admission rate of the fluid.

In this way, in the injection instrument of the present embodiment, a distance between each projection 12 of the hollow needle body 10 and the puncture target (e.g., skin) can be controlled by the fluid pressure caused by admitting the fluid into the deforming part 25. Therefore, after the distal end of each projection 12 of the hollow needle body 10 of the injection instrument punctures the skin, a puncture depth of the projection 12 into the puncture target can be easily changed while the puncture state is maintained.

<Another Embodiment>

Figure 7:
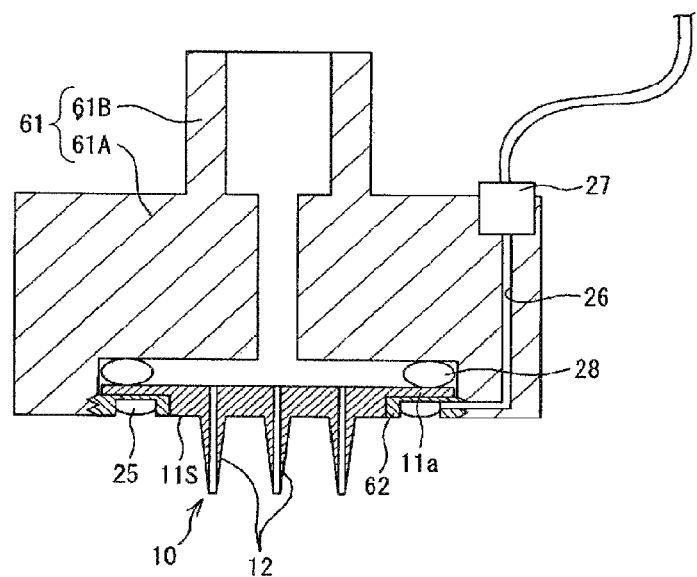
FIG. 7 is a schematic cross-sectional view of an injection instrument according to another mode of the present invention.
Figure 8:
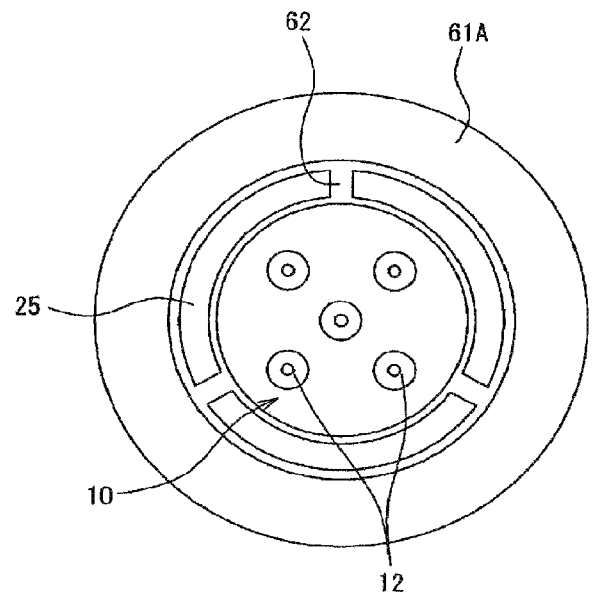
FIG. 8 is a schematic bottom view of the injection instrument according to another embodiment of the present invention.

FIGS. 7 and 8 illustrate another embodiment of the present invention.

As illustrated in FIGS. 7 and 8, another embodiment of the present invention is configured such that deforming parts 25 are arranged below a first surface 11S of a substrate 11. As illustrated in FIG. 7, in this mode, a channel is formed in a holder body 61A. In this mode, the holder body 61A and the outer peripheral member mentioned above are integrally formed, and the inward flange 22c mentioned above is separately formed to configure a deformation retaining part 62. In this example, the holder body 61A has a channel forming part and a fluid pressure applying part.

The deformation retaining part 62 is a ring-shaped plate member, and the deforming parts 25 are mounted to a recess 22b formed in a lower surface of the deformation retaining part 62. Each deforming part 25 is connected to the channel formed in the holder body 61A. The deformation retaining part 62 can be attached to or detached from the holder body 61A in such a manner that, for example, a male screw on an outer peripheral surface of the deformation retaining part 62 is threadably engaged with a female screw formed on a lower end of the holder body 61A. In this mode, the hollow needle body 10 is mounted from below.

As described above, the deforming part 25 is arranged outside a forming region of the projections 12, and on an outer peripheral side of the substrate 11 or a front side of the first surface 11S of the substrate 11. Therefore, the deforming part 25 can reliably bulge in a protruding direction of the projections 12, and the forming region of the plurality of projections 12 can be accurately spaced apart from the puncture target.

The deformation retaining part 62 is provided with a hole (through hole) that connects the channel 26 to the deforming part 25. The deformation retaining part is provided with the hole (through hole) so that when the male screw on the outer peripheral surface of the deformation retaining part 62 is threadably engaged with the female screw formed on the lower end of the holder body 61A, the channel 26 and the deforming part 25 are connected to each other in the threadably engaged state (tightened state).

The present inventors have confirmed that one of the causes of occurrence of liquid clogging and liquid leakage is that the hollow needle body 10 is pressed against the skin at the time of puncture performed by the hollow needle body 10, whereby swelling of the skin that accompanies the medicine administration is suppressed. The present inventors have also found that, in order to inhibit liquid leakage, it is important to release the state of the skin being pressed by the first surface 11S and the projections 12 of the hollow needle body 10. It has also been found to be effective that, to this end, the hollow needle body 10 is spaced apart from a surface of the skin by a specific distance while the puncture state of the hollow needle body 10 that has punctured the skin is maintained. This is one of the reasons why embodiments of the present invention have been made. The injection instrument according to an embodiment of the present embodiment can make the puncture depth shallow by deforming the deforming part 25 while maintaining the puncture state. Therefore, the skin can swell at the time of injection of the medicine, whereby the liquid clogging and the liquid leakage can be prevented.

A user of the injection instrument of the present embodiment can cause the projections 12 of the hollow needle body 10 to puncture the skin, followed by opening/closing a valve 27, thereby easily controlling millimeter-order or submillimeter-order translation of the projections 12 of the hollow needle body 10.

Examples of a switch mechanism of the valve 27 can include: a known latching mechanism that stops movement of a drive member by resisting against an energizing force from an energizing force generation source, not illustrated, (mechanism to release the energizing force by releasing a latch); a trigger mechanism (mechanism to release the energizing force by pulling a trigger); a pusher mechanism (mechanism to release the energizing force by pressing a pusher or a push button); and a manual/electromagnetically driven on-off valve capable of selectively supplying compressed gas from a compressed gas supply source including compressed air to a drive member, not illustrated.

The injection instrument of the present invention is preferably configured such that a distance (H2−H1), that can be controlled by the deformation of the deforming part 25, is 0.3 mm or more. The distance (H2−H1) that can be controlled by the deformation of the deforming part 25 is preferably equal to or less than a (needle height L of the hollow needle body 10+1 mm). If the distance (H2−H1) is less than 0.3 mm, the skin does not swell sufficiently at the time of injection of a medicine, and liquid leakage might occur. On the other hand, if the distance (H2−H1) exceeds the (needle height L of the hollow needle body 10+1 mm), the hollow needle body 10 is likely to detach from the skin. If the distance (H2−H1) is larger than the needle height L of the hollow needle body 10, the hollow needle body 10 does not detach from the skin since the skin follows the hollow needle body 10 as long as the distance (H2−H1) is the (needle height L of the hollow needle body 10+1 mm).

Figure 9:
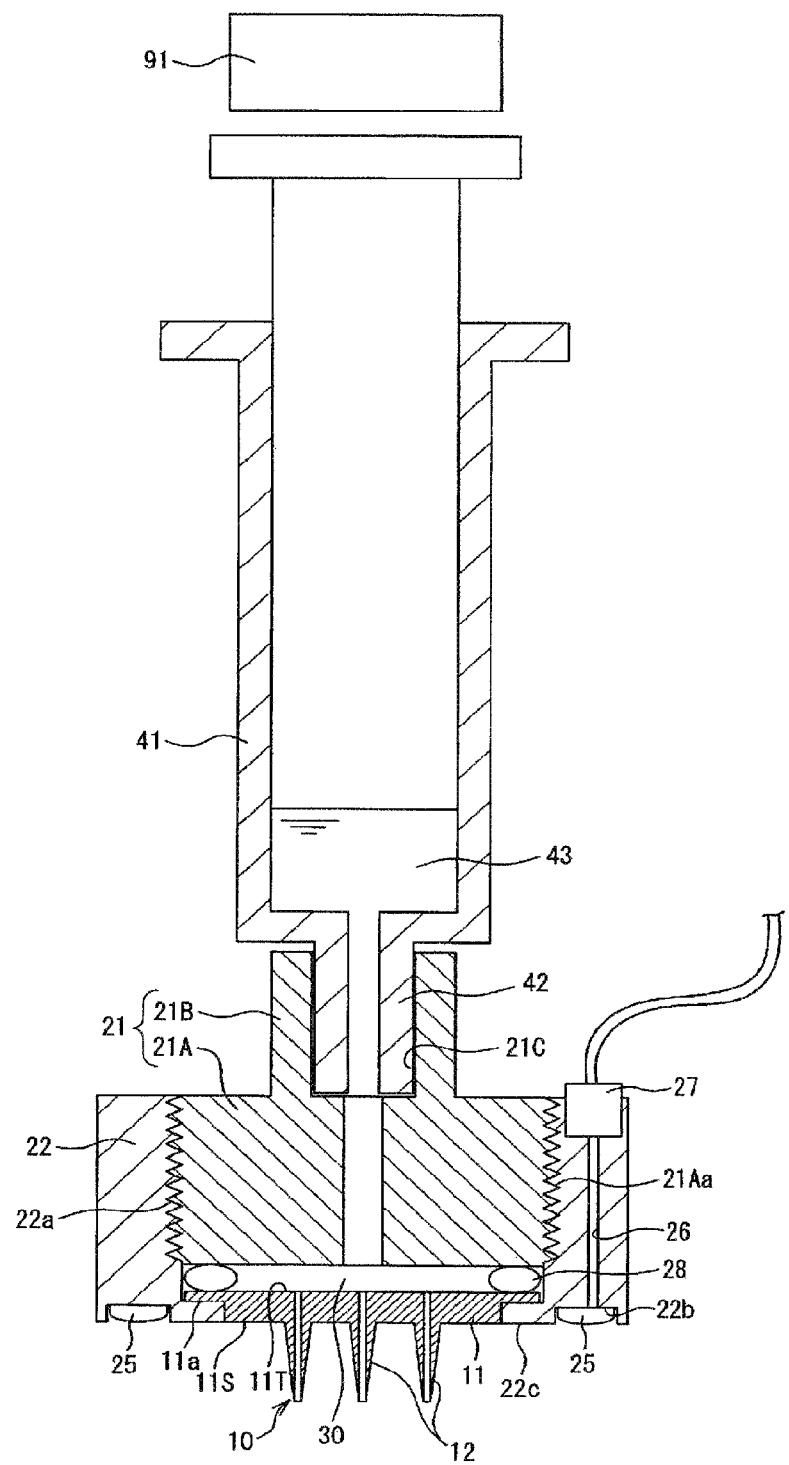
FIG. 9 is an explanatory view of a method of administering a medicine into skin using the injection instrument according to the embodiment of the present invention.

Besides the aforementioned mode, the intracorporeal injection liquid may be introduced using various puncture assisting instruments or a supply assisting device 91 (refer to FIG. 9). Such a supply device can be detachably fixed to a housing or a plunger of the injector, or an outer surface of the holder body 21A or the outer peripheral member 22 by a known fixing means, not illustrated, including, for example, a fixing screw and a clip. The supply device may be configured to selectively depress an externally exposed end of the plunger arranged being protruded as illustrated in FIG. 9. This configuration can include a drive member, not illustrated, an energizing force generation source, not illustrated, and a switch mechanism. The drive member abuts on or is brought close to the externally exposed end of the plunger. The energizing force generation source exerts, on the drive member, an energizing force toward the externally exposed end of the plunger. The switch mechanism causes the energizing force generation source to selectively generate the energizing force.

More specifically, for example, the energizing force generation source, not illustrated, can be selected from among a pressure compression spring, a tension spring, an elastic material, a magnet, or a supply source of pressure compressed gas including compressed air. Examples of the switch mechanism can include: a known latching mechanism that stops movement of a drive member by resisting against an energizing force from an energizing force generation source, not illustrated, (mechanism to release the energizing force by releasing a latch); a trigger mechanism (mechanism to release the energizing force by pulling a trigger); a pusher mechanism (mechanism to release the energizing force by pressing a pusher or a push button); and a manual/electromagnetically driven on-off valve capable of selectively supplying compressed gas from a compressed gas supply source including compressed air to a drive member (not illustrated).

Figure 10:
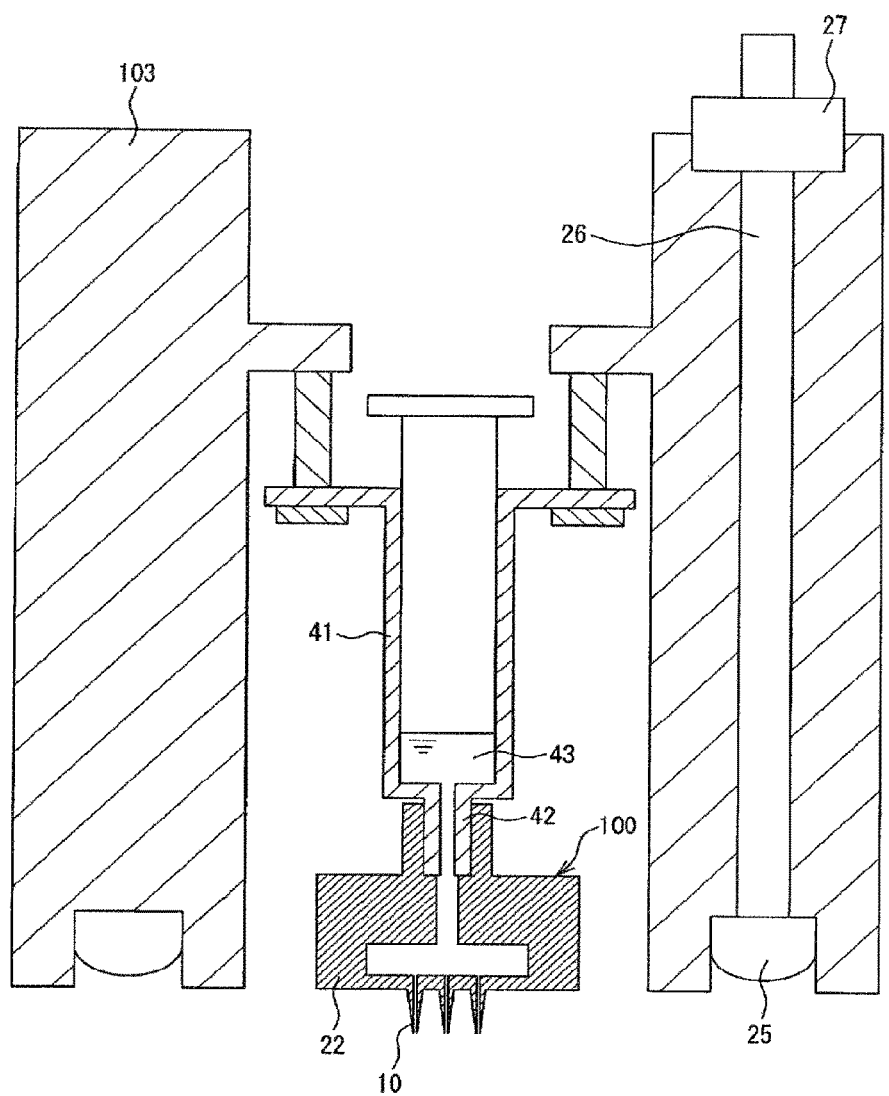
FIG. 10 is a schematic cross-sectional view of an injection instrument according to another mode of the present invention.
Figure 10:

FIG. 10 illustrates a schematic cross-sectional view of an injection instrument according to another embodiment of the present invention. FIG. 10 includes a hollow needle body 10 having the plurality of projections formed on the substrate, an outer peripheral member 22, and a hollow needle body (integrated type) 100 with which the holder is integrally formed. The hollow needle body (integrated type) 100 is connected to an injector 41. The injector 41 is fixed to a puncture assisting device 103 formed of a cylindrical body, and the puncture assisting device 103 includes a deforming part 25.

EXAMPLES

<Example>

Hereinafter, an example of the injection instrument according to an embodiment of the present invention will be described.

The following injection instrument having the structure illustrated in FIG. 4 was prepared.

Specifically, a hollow needle body 10, a holder 21 for holding the hollow needle body 10, and an outer peripheral member 22 were prepared. The hollow needle body 10 included a substrate 11 which was provided with nine projections 12, each being in a conical shape with a height of 2 mm. The hollow needle body 10 was made of polycarbonate and had an outer diameter of 10 mm. The holder 21 was made of polycarbonate. The outer peripheral member 22 had the channel and a deforming part 25 made of natural rubber within a housing made of polycarbonate. An O-ring made of silicone was used to form a liquid-tight structure and the chamber 30 between the hollow needle body 10 and the holder body 21A. Compressed air was used as a fluid supplied into the outer peripheral member 22. The compressed air was supplied into the outer peripheral member 22 for 1 minute under the atmospheric pressure and under a pressure condition of 110 kPa, whereby the H2 was increased to 1 mm.

Water dyed blue was prepared as an alternative to the intracorporeal injection liquid (medicine). An artificial skin was punctured with a load of 2 kgf in a state where there was no admission of fluid into the pressure channel 26. After the load is relieved, with the supply of the compressed air, the hollow needle body 10 was lifted up until a distance between the first surface 11S of the hollow needle body 10 and the artificial skin became 0.5 mm. At this time, the projections 12 of the hollow needle body 10 did not detach from the artificial skin.

Next, a piston was pushed to inject the blue liquid into the artificial skin, followed by microscopic observation. Leakage of the injected liquid was not observed on the surface of the artificial skin.

<Comparative Example>

The same injection instrument as that of the Example described above was prepared.

However, the outer peripheral member 22 was not operated. In other words, the fluid was not admitted into the pressure channel 26, and the fluid pressure was not generated.

Water dyed blue was prepared as an alternative to the intracorporeal injection liquid. An artificial skin was punctured with a load of 2 kgf. Next, the piston was pushed with the same strength as that of the above Example to inject the blue liquid into the artificial skin, but the piston could not be pushed due to internal resistance. Furthermore, when a force was applied to push the piston, leakage of the liquid to the surface of the artificial skin was observed. The liquid that had leaked to the surface was wiped off for microscopic observation of the surface of the artificial skin. As a result, it was found that blue liquid had hardly been injected into the artificial skin.

The present invention has been described so far with reference to the specific embodiments. However, the invention should not be construed as being limited by the description. By referring to the description of the present invention, a person skilled in the art would obviously variously modify the disclosed embodiment and other embodiments of the present invention. Therefore, the claims should be construed as covering these modifications or embodiments which are encompassed by the scope and spirit of the present invention.

The injection instruments according to the foregoing embodiments can solve the technical problem addressed by the present application. The aforementioned technical problem addressed by the present application will be described in detail.

Administration of a medicine such as a vaccine into a living body performed by an injection has been widely established. Although injections are a highly safe administration method, most of the injections are likely to be accompanied by strong pain since an injection needle punctures a living body deeply for the administration of the medicine into hypodermis. In addition, in developing countries infection and needle piercing accidents caused by reuse of injection needles constantly occur.

In this regard, as a medicine administration method that is an alternative to an injection, attention is being paid to a method of administering a medicine into skin by puncturing the skin using an array component including a large number of micron-order projections as described in Patent Literature 1. According to this method, the length of the needle body is set to such a length that the needle body does not reach nerve cells in a dermic layer, whereby a painful sensation can be almost completely prevented at the time of the puncture into the skin.

Furthermore, when a vaccine is intradermally administered using the needle body, the vaccine is administered into the skin where there is an abundance of antigen-presenting cells. Therefore, the amount of vaccine to be used may be reduced compared with a subcutaneous injection.

A shape of the needle body needs to be sufficiently thin and have a distal end angle suitable for puncturing the skin, and a length sufficient for causing a medicine to permeate into the skin. Therefore, it is considered to be desirable that the needle body has a diameter of several tens of μm to several hundred μm and has such a length that the needle body penetrates a cornified layer, i.e., the outermost layer of the skin, but does not reach a neural layer, and specifically has a length of about several hundred μm to several mm.

Several methods have been considered as a method of intradermally administering a medicine using a needle body, examples of which include: a method of applying a medicine to a surface of the skin before or after causing a needle body to puncture the skin; a method of causing a needle body with a medicine applied to its surface in advance to puncture the skin; and a method of causing a hollow needle body, that is a needle body provided with a through hole, to puncture the skin and administering a medicine into the skin by way of the through hole.

Compared with other methods, the administration method using the hollow needle body having a through hole is advantageous in that a liquid dosage form can be utilized and a medicine dose can be easily adjusted in the same way as a conventional subcutaneous injection, but has such a problem that a portion of the medicine is likely to leak to the surface of the skin.

As a measure to prevent liquid leakage, for example, Patent Literature 2 proposes an injection drug delivery device including a needle, a limiter, and a rigid stabilizer. Specifically, the limiter controls an insertion depth of the needle, and the rigid stabilizer prevents distortion, pressure contraction, or thinning of a tissue in the vicinity of the needle insertion part. However, since it is difficult for this device to include a plurality of needles, the device has such a problem that a medicine dose is limited.

(Effects of Present Embodiment)

(1) As compared with the conventional technique having the problem stated above, the injection instrument according to the present embodiment includes: the hollow needle body 10 having one or more projections 12 on the first surface 11S of the substrate 11, with the through hole 13 penetrating from the distal end side of each projection 12 to the second surface 11T of the substrate 11 being formed in each of the projections 12; the deforming part 25 arranged outside a region in which the projections 12 are formed, the deforming part 25 being deformable so as to bulge in a projecting direction of the projections 12 beyond a plane that is flush with the first surface 11S on which the projections 12 are formed; and the pressure channel 26 causing the fluid to apply a fluid pressure to the deforming part 25. The deforming part 25 is deformed in the projecting direction of the projections 12 in response to the fluid pressure.

With this configuration, the deforming part 25 is deformed after the hollow needle body 10 forming the injection instrument has punctured the skin, whereby the hollow needle body 10 can be lifted up from the skin by a suitable distance. Therefore, a medicine can be administered without inhibiting swelling of the skin. As a result, the medicine is reliably administered into the skin while inhibiting leakage of the medicine to the surface of the skin.

In addition, with the injection instrument according to each of the foregoing embodiments, a plurality of projections (needle structures) 12 can be provided on the hollow needle body 10, and thus a medicine dose can be increased.

(2) The injection instrument according to the present embodiment may include the holder 21 or 61 having the medicine channel 21C configured to guide a medicine to be injected through the projections 12 to the second surface 11T side of the substrate 11. The pressure channel 26 may be arranged on an outer peripheral side of the medicine channel 21C.

With this configuration, the degree of freedom for arranging the channel 26 to the deforming part 25 can be enhanced.

(3) The injection instrument according to the present embodiment may be configured such that the deforming part 25 is arranged on an outer peripheral side of the substrate 11 or a front side of the first surface 11S of the substrate 11.

With this configuration, the deforming part 25 can reliably bulge in the protruding direction of the projections 12, and the forming region of the plurality of projections 12 can be spaced apart from the puncture target with high accuracy.

(4) The injection instrument according to the present embodiment may be configured such that the fluid pressure is generated by a warming medium fluid.

With this configuration, relaxation of the skin can be accelerated. Therefore, swelling of the skin at the time of injecting a liquid can be accelerated.

(5) The injection instrument according to the present embodiment may be configured such that the fluid pressure is generated by a cooling medium fluid.

With this configuration, the skin can be tensed. Therefore, when the injection instrument of the present embodiment punctures the skin, the puncture can be reliably performed.

(6) The injection instrument according to the present embodiment may be configured such that the hollow needle body 10 is formed of a material having biocompatibility.

With this configuration, if the hollow needle body 10 is broken and remains within a human body, the influence on the human body can be minimized.

(7) The injection instrument according to the present embodiment may be configured such that the height from the first surface 11S to the top of each projection 12 is within the range of 0.3 mm or more to 2.0 mm or less.

With this configuration, the projections 12 do not reach nerve cells in a dermic layer, whereby pain felt by the patient at the time of puncturing the skin can be reduced.

(8) The injection instrument according to the present embodiment may be configured such that, when the height from the first surface 11S to the top of each projection 12 is L (mm), the deforming part 25 is deformed in the projecting direction of the projection 12 in response to the fluid pressure so as to have a height in a range of 0.3 mm or more to L+1 mm or less from the first surface 11S.

With this configuration, the puncture depth can be reduced and thus the skin can swell at the time of injecting a medicine, whereby liquid clogging and liquid leakage can be prevented.

With regard to Patent Literature 2 (JP-A-2009-516572), it is difficult for a device described in Patent Literature 2 to include a plurality of needles. Therefore, the device described in Patent Literature 2 has a problem that a medicine dose is limited.

In one aspect, the present invention can provide an injection instrument for administering a medicine into the skin more reliably while inhibiting leakage of the medicine to the surface of the skin, when the medicine is intradermally administered using a hollow needle body.

In order to solve the problem set forth above, an injection instrument according to an aspect of the invention is characterized in that the instrument includes: a hollow needle body having one or more projections on a first surface of a substrate, each projection being formed with a through hole penetrating from a distal end thereof to a second surface that is the other surface of the substrate; deforming part arranged outside a region in which the one or more projections are formed, the deforming part being deformable so as to bulge in a projecting direction of the projections beyond a plane that is flush with the first surface on which the projection is formed; and a pressure channel that causes a fluid to apply a fluid pressure to the deforming part, wherein the deforming part is deformable in the bulging direction in response to the fluid pressure.

In an injection instrument according to an aspect of the present invention, the deforming part is deformed after a hollow needle body of the injection instrument has punctured the skin, whereby the hollow needle body can be lifted up from the skin by a suitable distance. Therefore, a medicine can be administered in a state where swelling of the skin is not suppressed. As a result, the medicine is reliably administered into the skin while inhibiting leakage of the medicine to the surface of the skin.

In the injection instrument according to an aspect of the present invention, a plurality of projections (needle structures) can be provided on the hollow needle body, whereby a medicine dose can be increased.

REFERENCE SIGNS LIST 10 hollow needle body
11 substrate
11a step
11S first surface
11T second surface
12 projection
13 through hole
21, 61 holder
21A holder body
21B connection part
21C medicine channel
22 outer peripheral member
22a female screw
25 deforming part
26 pressure channel
27 valve
28 liquid tight member
30 chamber
41 injector
42 injector attachment projection
43 intracorporeal injection liquid
51 puncture target
62 deformation retaining part
100 hollow needle body (integrated type)
103 puncture assisting device Obviously, numerous modifications and variations of the present invention are possible in light of the above teachings. It is therefore to be understood that within the scope of the appended claims, the invention may be practiced otherwise than as specifically described herein.

What is claimed is:

1. An injection instrument, comprising:
a hollow needle body including a substrate having a first surface and a second surface opposite to the first surface, the hollow needle body having at least one projection which is formed on the first surface and has a through hole penetrating from a distal end of the at least one projection to the second surface of the substrate;
a deforming member positioned outside an outer periphery of the first surface of the substrate such that the deforming member is configured to deform and bulge in a bulging direction along a projecting direction of the at least one projection; and
an outer peripheral member having a recess in which the deforming member is positioned, and a pressure channel through which a fluid is supplied to the deforming member such that a fluid pressure is applied to the deforming member and that the deforming member deforms in the bulging direction in response to the fluid pressure,
wherein the outer peripheral member has the recess having an opening in the projecting direction of the at least one projection and is configured to hold the hollow needle body such that the deforming member in the recess is positioned outside the outer periphery of the first surface of the substrate and bulges outward from the opening of the recess and beyond a plane flush with the first surface of the substrate when the fluid pressure is applied to the deforming member.

2. The injection instrument of claim 1, further comprising:
a holder having a medicine channel through which a medicine is supplied to and injected through the through hole of the at least one projection from the second surface of the substrate,
wherein the pressure channel is formed in the outer peripheral member on an outer peripheral side of the medicine channel of the holder.

3. The injection instrument of claim 1, wherein the outer peripheral member is formed such that the deforming member is positioned on an outer peripheral side of the substrate or a front side of the first surface of the substrate.

4. The injection instrument of claim 2, wherein the outer peripheral member is formed such that the deforming member is positioned on an outer peripheral side of the substrate or a front side of the first surface of the substrate.

5. The injection instrument of claim 1, wherein the deforming Member is configured to deform and bulge in response to the fluid pressure generated by a warming medium fluid.

6. The injection instrument of claim 1, wherein the deforming member is configured to deform and bulge in response to the fluid pressure generated by a cooling medium fluid.

7. The injection instrument of claim 1, wherein the hollow needle body comprises a material having biocompatibility.

8. The injection instrument of claim 2, wherein the hollow needle body comprises a material having biocompatibility.

9. The injection instrument of claim 3, wherein the hollow needle body comprises a material having biocompatibility.

10. The injection instrument of claim 4, wherein the hollow needle body comprises a material having biocompatibility.

11. The injection instrument of claim 1, wherein the hollow needle body is configured such that a height from the first surface to a top of the at least one projection is within a range of front 0.3 mm to 2.0 mm.

12. The injection instrument of claim 2, wherein the hollow needle body is configured such that a height from the first surface to a top of the at least one projection is within a range of from 0.3 mm to 2.0 mm.

13. The injection instrument of claim 3, wherein the hollow needle body is configured such that a height from the first surface to a top of the at least one projection is within a range of from 0.3 mm to 2.0 mm.

14. The injection instrument of claim 4, wherein the hollow needle body is configured such that a height from the first surface to a top of the at least one projection is within a range of from 0.3 mm to 2.0 mm.

15. The injection instrument of claim 1, wherein the deforming member is configured to deform and bulge in a range of from 0.3 mm to L+1 mm from the first surface in the bulging direction in response to the fluid pressure, where L is a height in mm from the first surface to a top of the at least one projection.

16. The injection instrument of claim 2, wherein the deforming member is configured to deform and bulge in a range of from 0.3 mm to L+1 mm from the first surface in the bulging direction in response to the fluid pressure, where L is a height in mm from the first surface to a top of the at least one projection.

17. The injection instrument of claim 3, wherein the deforming member is configured to deform and bulge in a range of from 0.3 mm to L+1 mm from the first surface in the bulging direction in response to the fluid pressure, where L is a height in mm from the first surface to a top of the at least one projection.

18. The injection instrument of claim 4, wherein the deforming member is configured to deform and bulge in a range of from 0.3 mm to L+1 mm from the first surface in the bulging direction in response to the fluid pressure, where L is a height in mm from the first surface to a top of the at least one projection.

19. The injection instrument of claim 2, wherein the outer peripheral member has an inward flange configured to engage with an outer periphery of the substrate of the hollow needle body, and the holder comprises a holder body configured to attach to the outer peripheral member.

20. The injection instrument of claim 19, wherein the holder body has a connection part configured to attach an injection needle attachment projection of an injector.

* * * * *